United States Patent [19]
Rock et al.

[11] Patent Number: 6,022,529
[45] Date of Patent: Feb. 8, 2000

[54] PHOTORESPONSIVE SUNSCREEN COMPOSITIONS

[75] Inventors: Ronald S. Rock; Michael H. B. Stowell, both of Pasadena, Calif.

[73] Assignee: California Institute of Technology, Pasadena, Calif.

[21] Appl. No.: 08/907,188

[22] Filed: Aug. 6, 1997

[51] Int. Cl.$^7$ .............................. A61K 7/42; A61K 7/00
[52] U.S. Cl. .............................. 424/59; 424/60; 424/400; 424/401
[58] Field of Search ............................. 424/89, 60, 400, 424/401

[56] References Cited

U.S. PATENT DOCUMENTS

| | | |
|---|---|---|
| 3,702,854 | 11/1972 | Jurd . |
| 3,901,908 | 8/1975 | Fitzi et al. . |
| 4,469,774 | 9/1984 | Lee .......................................... 430/270 |
| 4,822,600 | 4/1989 | Wortzman ................................. 424/59 |
| 5,200,334 | 4/1993 | Dunn et al. .............................. 435/182 |

FOREIGN PATENT DOCUMENTS 2 285 854  12/1974  France .

OTHER PUBLICATIONS

Pirrung, M.C., et al., "Dimethoxybenzoin Carbonates: Photochemically–Removable Alcohol Protecting Groups Suitable for Phosphoramidite–Based DNA Synthesis", *J. Org. Chem.* 60:1116–1117 (1995).

Gurney, A.M., et al., "Light–Flash Physiology with Synthetic Photosensitive Compounds", *Physiological Reviews* 67(2):583–617 (1987).

Pillai, V.N.R., "Photoremovable Protecting Groups in Organic Synthesis", *Reviews* pp. 1–27 (1980).

Cameron, J.F., et al., "New Photolabile Amino Protecting Groups: Photogeneration of Amines from [(3', 5'–Dimethoxybenzoinyl)oxy]carbonyl Carbamates", *J. Chem. Soc., Chem. Commun.* pp. 923–924 (1995).

Pirrung, M.C., et al., "Photoremovable Protecting Groups for Phosphorylation of Chiral Alcohols. Asymmetric Synthesis of Phosphotriesters of (–)–3',5'–Dimethoxybenzoin" *J. Org. Chem.* 59:3890–3897 (1994).

McCray, J.A., et al., "Properties and Uses of Photoreactive Caged Compounds", *Annu. Rev. Biophys. Biophys. Chem.* 18:239–270 (1989).

Cummings, R.T., et al., "Photoactivable Fluorophores. 1. Synthesis and Photoactivation of o–Nitrobenzyl–Quenched Fluorescent Carbamates", *Tetrahedron Letters* 29(1):65–68 (1988).

Mendel, D., et al., "Construction of a Light–Activated Protein by Unnatural Amino Acid Mutagenesis", *J. Am. Chem. Soc.* 113:2578–2760 (1991).

Baldwin, J.E., et al., "New Photolabile Phosphate Protecting Groups", *Tetrahedron* 46 19:6879–6884 (1990).

Corrie, J.E.T., et al., "Synthetic, Mechanistic and Photochemical Studies of Phosphate Esters of Substituted Benzoins", *J. Chem. Soc. Perkin Trans 1* pp. 2409–2417 (1992).

Pirrung, M.C., et al., "Photochemical Deprotection of 3'–5'–Dimethoxybenzoin(DMB) Carbamates Derived from Secondary Amines", *Tetrahedron Letters* 36(33):5883–5884 (1995).

(List continued on next page.)

*Primary Examiner*—Shelley A. Dodson
*Attorney, Agent, or Firm*—Flehr Hohbach Test Albritton & Herbert LLP; Richard F. Trecartin

[57] ABSTRACT

The disclosure provides sunscreen compositions comprising a carrier for topical administration and photoresponsive first sunscreen agents which are capable of undergoing intramolecular photorearrangements to form second sunscreen agents. The second sunscreen agents absorb more ultraviolet radiation than the first sunscreen agents. The sunscreen composition may comprise the prephotorearrangement first sunscreen agent, the photorearranged second sunscreen agent, a combination of the first and second sunscreen agents, or any of the above in combination with a known sunscreen agent.

14 Claims, 3 Drawing Sheets

OTHER PUBLICATIONS

Sheehan, J.C., et al., "The Photolysis of Methoxy–Substituted Benzoin Esters. A Photosensitive Protecting Group of Carboxylic Acid", *Journal of the American Chemical Society* 93 (26):7222–7228 (1971).

Krepski, L.R., et al., "Addition of Grignard Reagents to O–Trimethylsilylated Cyanohydrins: Synthesis of Acyloins", *Angew. Chem. internat. Edit* 4(12):4075 (1965).

Rajaserharan Pillai, V.N., "Photoremovable Protecting Groups in Organic Synthesis," Synthesis, 1–27 (Jan. 1980).

Abstracts, Angew. Chem. Internat. Edit., 4(12) 1075–1078 (1965).

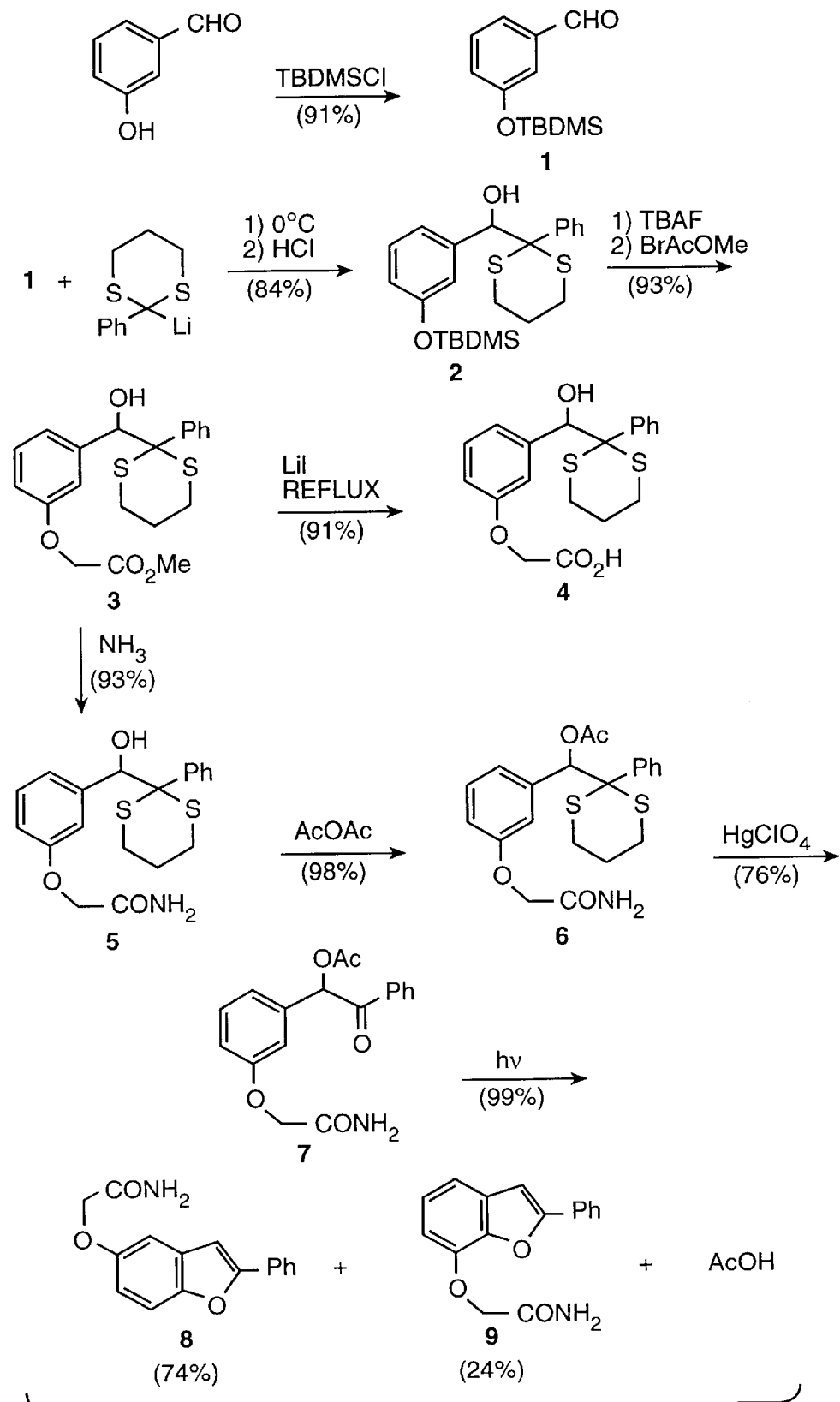
FIG._1

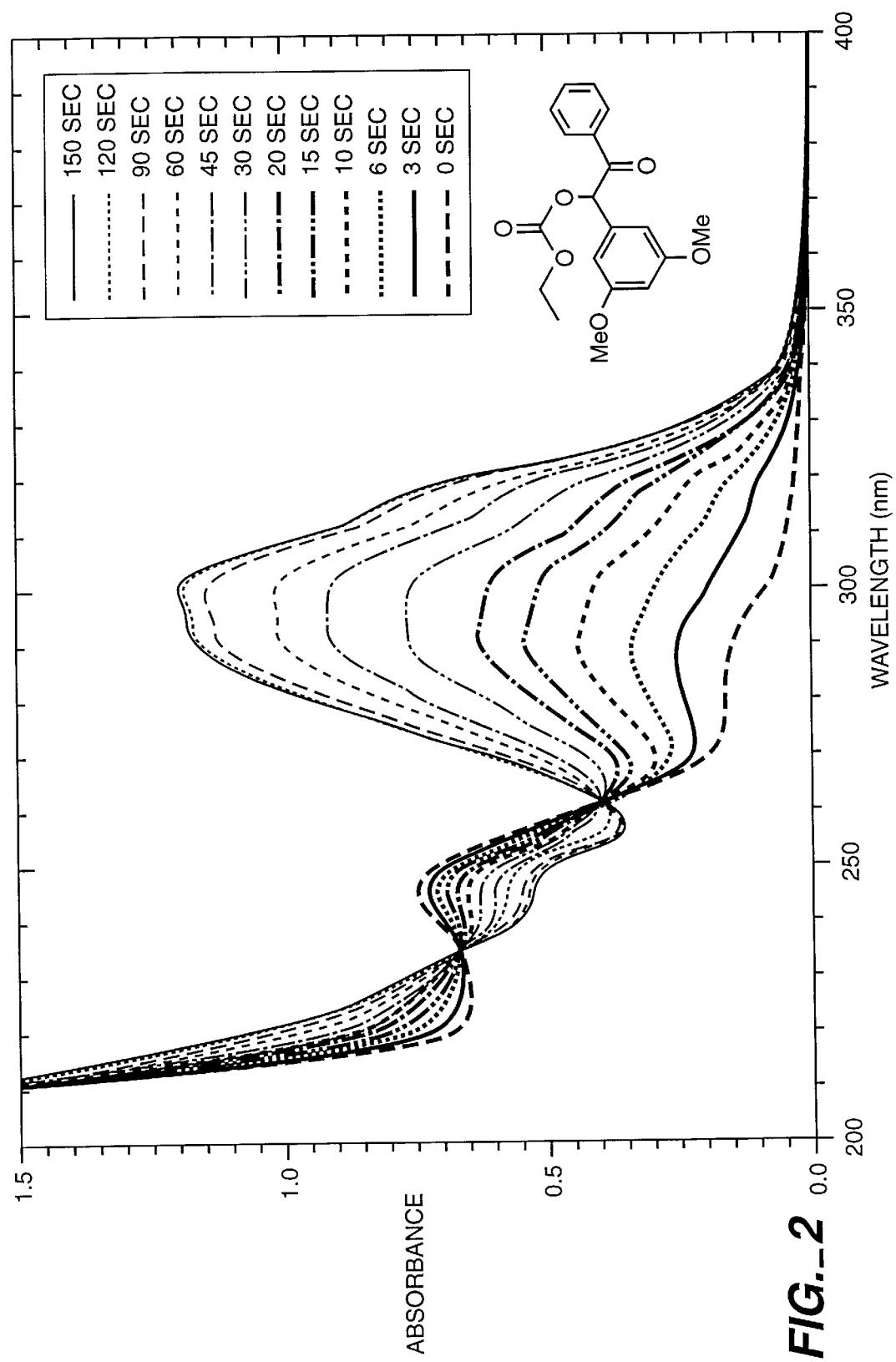
FIG._2

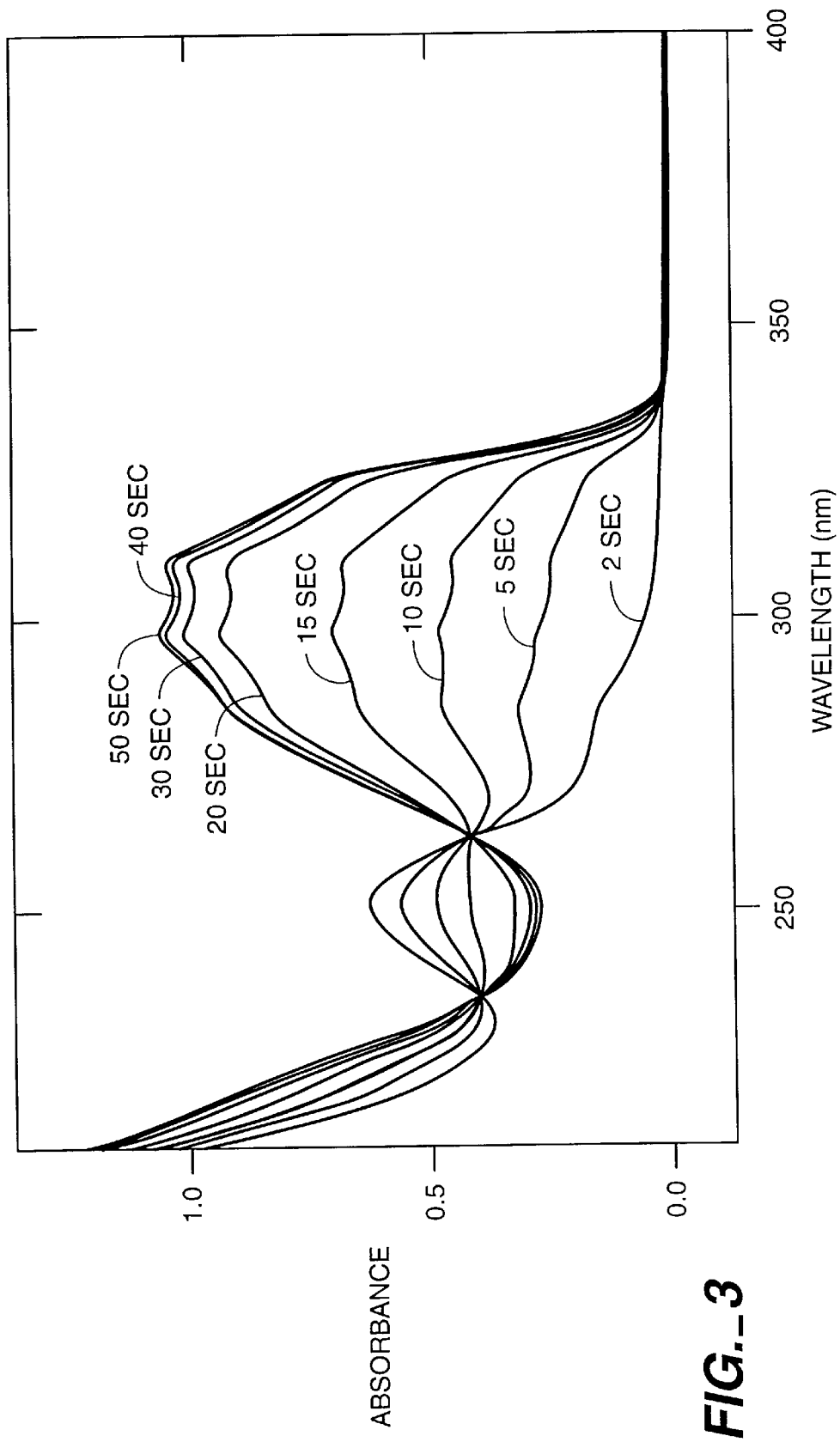
FIG._3

PHOTORESPONSIVE SUNSCREEN COMPOSITIONS

FIELD OF THE INVENTION

This invention relates to photoresponsive sunscreen compositions, and more particularly, to compositions for protecting skin or hair from sunlight comprising a carrier for topical administration and an organic sunscreen agent capable of undergoing efficient photorearrangement converting the sunscreen agent molecules from weak to strong ultraviolet-absorbing compounds.

BACKGROUND OF THE INVENTION

Overexposure to sunlight can cause premature aging of the skin and in some circumstances can lead to skin cancer. One method of preventing such skin damage is to avoid more than limited exposure to sunlight. An alternative preventive method involves the widespread use of commercially-available sunscreen compositions.

Sunscreen compositions come in a wide array of formulations including those which are preformulated to give a particular level of protection based upon an expected exposure to sunlight. The drawback with such formulations is that the user may become overexposed if the expected exposure level is underestimated.

Therefore, it is an object of this invention to provide a composition for protection from ultraviolet radiation, typically in the form of sunlight, comprising a photoresponsive element which adjusts the level of protection according to the exposure of radiation received by the user.

It is also an object of this invention to provide sunscreen compositions comprising organic molecules which undergo an efficient photoreaction, converting the molecule from a weakly-absorbing compound to a strongly-absorbing compound.

It is also an object to provide a method for obtaining protection from UV-A/B/C light through the use of compositions comprising derivatives of benzoins which which undergo photolysis when exposed to UV-A/B/C light and yield benzofurans with large extinction coefficients in the UV-A/B/C region of the electromagnetic spectrum.

SUMMARY

A novel use for photoactive compounds as ingredients in a photoresponsive sunscreen composition is described herein. In particular, compositions for protecting skin or hair from ultraviolet radiation are described herein which comprise a carrier for topical administration and an organic sunscreen agent which undergoes an efficient photoreaction converting the agent from a weak ultraviolet-absorbing compound into a strong ultraviolet-absorbing compound.

As demonstrated herein, one example of this type of molecule is the acetyl ester of 3',5'-dimethoxybenzoin.

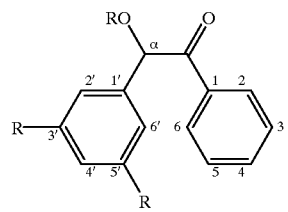

Formula 1. The generic structure and numbering scheme for 3', 5'-disubstituted benzoin esters.

BRIEF DESCRIPTION OF THE DRAWINGS

FIG. 1 depicts the synthesis of exemplary compounds of the invention.

FIG. 2 is an ultraviolet spectrograph showing the steady-state photolysis of 3',5'-dimethoxybenzoin ethyl carbonate from 0 to 150 seconds. A 53.5 $\mu$M solution of the benzoin derivative in acetonitrile was irradiated with an Oriel 66011 Hg vapor lamp using UG11 and WG320 filters.

FIG. 3 is an ultraviolet spectrograph showing the steady-state photolysis of ($\pm$)-O-acetyl-3'-carbamylmethoxybenzoin. A 54.8 $\mu$M solution of ($\pm$)-O-acetyl-3'-carbamylmethoxybenzoin in 1:1 methanol/Tris·HCl (0.05 M, pH 7.4) was irradiated with an Oriel 66011 Hg vapor lamp using UG11 and WG320 filters.

DETAILED DESCRIPTION OF THE INVENTION

Described herein are sunscreen compositions and methods of using sunscreen compositions which comprise a photoresponsive sunscreen agent and a carrier for topical administration of the sunscreen agent.

As is generally known in the art, sunscreen compositions typically contain sunscreen agents, which individually or collectively absorb specific wavelengths of light over a large portion of the ultraviolet region of the electromagnetic spectrum. More specifically, most previously-known sunscreen compositions contain one or more ultraviolet-absorbing compounds that act as filters of electromagnetic radiation covering parts or all of the UV-A (320–400 nm) and UV-B (290 to 320 nm) segments of the ultraviolet spectrum.

A large variety of well-known ultraviolet-absorbing compounds have been used, alone or in combination, in various sunscreen compositions. These compositions have been found to provide varying sun protection factors (SPFs) when evaluated in human subjects utilizing standard solar simulator tests. The sunscreen agents act to block the passage of erythemogenic radiation, by absorption, thereby preventing its penetration into the skin.

Described herein is the novel use of photoresponsive compounds as new sunscreen agents. Preferred photoresponsive sunscreen agents are weakly ultraviolet-absorbing and are capable of undergoing intramolecular photorearrangements to form compounds which are strongly ultraviolet-absorbing. These photolabile compounds can be used in sunscreen compositions to provide at least one element whose sunscreening protection increases with the amount of light present. The sunscreen agents can be used alone or in combination with known sunscreen agents.

Many photolabile compounds are currently available. Compounds having photolytic properties, including benzoin esters of carboxylates and phosphates (Corrie, et al., J.

Chem. Soc. Perkin. Trans., 1:2409 [1992]; Pirrung et al. J. Org. Chem., 59:3890 [1994]) have been described and are known in the art.

One class of photolabile compounds are the substituted benzoins initially reported by Sheehan et al., J. Am. Chem. Soc. 93:7222 (1971). Of particular interest are the substituted alkoxybenzoins which have quite remarkable photocleavage properties. Some examples are the 3',5'-dimethoxybenzoin esters (3',5'-DMB) which undergo a photoinitiated cyclization and cleavage as shown in Equation 1. This reaction has a rate constant estimated to be greater than $10^{10}$ sec$^{-1}$ and a quantum efficiency of 0.64, when RO— on the α carbon (Equation 1) is acetyl. FIG. 2 shows steady-state photolysis results for 3',5'-dimethoxybenzoin ethyl carbonate. FIG. 3 shows steady-state photolysis results for O-acetyl-3'-carbamylmethoxybenzoin. Both graphs show a dramatic increase in the $\epsilon_{max}$ values between 260 and 350 nm as the compounds undergo a photorearrangement from the benzoin structures to benzofiran structures.

Equation 1

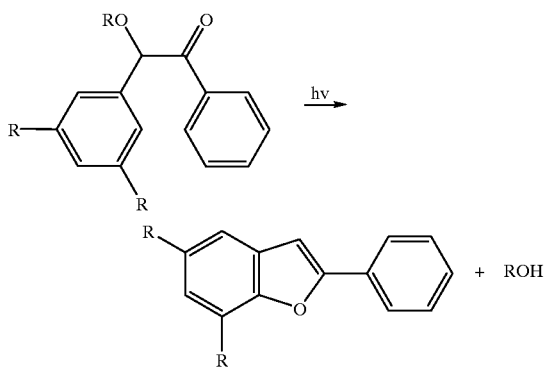

Other preferred sunscreen agents include those having low maximum extinction coefficients ($\epsilon_{max}$) in the UV-A/B/C region of the electromagnetic spectrum, preferably between 260 and 350 mn, prior to photolysis, and a larger $\epsilon_{max}$ over the same range following photolysis. Preferably, this transformation takes place through an intramolecular photochemical rearrangement.

An increase in the sunscreen agent's $\epsilon_{max}$ after photolysis is only one measure of increased sunscreen activity. The $\epsilon_{max}$ indicates only the height of an absorption band. Absorption bands having the same $\epsilon_{max}$ may have different activities depending on if the absorption band is narrow or broad. A more accurate measure of a sunscreen agent's activity involves calculating the total area occupied by the absorption band. Determination of the area encompassed by an absorption band can be accomplished by several methods, including the use of a built-in integrator on an ultraviolet spectraphotometer, or simply plotting the spectra and cutting out and weighing the bands. Preferred sunscreen agents have low-area bands in the UV-A/B/C region of the electromagnetic spectrum, preferably between 260 and 350 nm, prior to photolysis, and show an increase in band area over the same range following photolysis.

In one preferred embodiment, the compositions comprise a first sunscreen agent which undergoes efficient, intramolecular photorearrangement, initiated by ultraviolet radiation, preferably between about 250 and about 400 nm, to form a second sunscreen agent which absorbs more ultraviolet radiation, preferably between about 250 and about 400 nm, most preferably between about 260 and about 350 nm. Such first sunscreen agents preferably have at most a weak $\epsilon_{max}$ between about 250 and about 400 nm before photolysis and a comparatively stronger $\epsilon_{max}$ between 250 and 400 nm following photolysis.

The compositions may further comprise traditional sunscreen agents as auxiliary sunscreen agents for optimal sunscreen composition properties. In a preferred embodiment, photorearrangement rates are adjusted by including additives that compete for light.

Certain photolabile compounds, such as benzoin derivatives, are capable of undergoing intramolecular photorearrangements forming new compounds which absorb more radiation in the UV-A, -B or -C regions. The rate with which the photorearrangement occurs for these compounds can be controlled by the substituent R groups of the compound. Additionally, the wavelength ranges over which the higher-absorbing rearrangement product absorbs varies according to the type and position of the substituents on the compound. This allows for the tailoring of such compounds to filter out light over broad wavelength regions either individually or in combination with other sunscreen agents within the scope of the invention or sunscreen agents previously described in the art.

Preferred sunscreen compositions comprise photoresponsive sunscreen agents and a carrier for topical administration—aiding in the application of appropriate amounts of sunscreen agent to the skin. For topical application, sunscreen compositions are preferably nontoxic and nonirritating to the skin tissue.

Preferred sunscreen compositions may be in the form of creams, gels, lotions, oils, or other solutions comprising as the active agents prephotolysis compounds (Formula 3), postphotolysis compounds (Formula 4), or a combination of the two. The compositions are preferably formulated using homogeneous solutions, such as anhydrous solvents, or heterogeneous mixtures, such as emulsions. Topical carriers and general methods of formulation and manufacture of sunscreen compositions are known in the art See U.S. Pat. Nos. 4,522,807 and 4,822,600, expressly incorporated herein by reference.

Examples of suitable topical carriers are, but are not limited to, water, lower monoalcohols as well as their mixtures, or aqueous alcoholic or oil/alcohol solutions, the preferred alcohols being selected from the group consisting of ethanol, isopropyl alcohol, propylene glycol, glycerol, and sorbitol, and the preferred aqueous alcoholic mixtures being mixtures of water and ethyl alcohol.

In addition to a carrier element to aid in distribution of the photoresponsive sunscreen agent onto the skin, some embodiments may include additives to improve the cosmetic properties of the sunscreen composition. Some cosmetic ingredients which may be used include: thickeners, softeners, superfatting agents, waterproofing agents, emollients, wetting agents, and surface-active agents, as well as preservatives, anti-foam agents, fragrance, or any other compatible ingredient usually employed in cosmetics.

The following film-forming agents and cosmetic resins are also useful in the practice of the present invention, namely: polyvinylpyrrolidone; vinylpyrrolidone/vinyl acetate copolymers in which the monomers ratios are from 70:30 to 30:70; vinyl acetone/unsaturated carboxylic acid copolymers such as a copolymer containing 90% of vinyl acetate and 10% of crotonic acid, terpolymers of methyl methacrylate/stearyl methacrylate/dimethylaminoethyl methacrylate, completely quaternised with dimethyl sulfate, the monomers being used particularly in the ratio 20:23:57, and a terpolymer of vinyl acetate/allyl stearate/allyloxyacetic acid, especially in the ratio of 80:15:5, maleic anhydride/methyl vinyl ether copolymers such as those commercially referred to as "Gantrex AN" as well as the ethyl, isopropyl, and butyl esters of these copolymers, and maleic anhydride/butyl vinyl ether copolymers.

In addition to the carrier for topical administration, photoresponsive sunscreen compositions may comprise individual photoresponsive sunscreen agents, combinations of two or more photoresponsive sunscreen agents of the invention, or combinations of one or more photoresponsive sunscreen agents with one or more known sunscreen agents. Optimally, if a mixture of sunscreen agents is used, the mixture will cover a broad wavelength band of the ultraviolet spectrum.

The photoresponsive sunscreen agents of this invention may be combined with one or more known, nonphotorearranging sunscreen agents. Preferable known, ultraviolet-absorbing compounds include: oxybenzone (2-hydroxy-4-methoxybenzophenone); dioxybenzone (2,2'-dihydroxy-4-methoxybenzophenone); amino benzoic acid; cinoxate (2-ethoxyethyl-p-methoxycinnamate); diethanolamine p-methoxycinnamate; digalloyl triolcate ethyl 4-bis (hydroxypropyl)aminobenzoate; 2-ethylhexyl 2-cyano-3,3-diphenylacrylate; 2-ethylhexyl p-methoxycinnamate; 2-ethylhexyl salicylate; glyceryl aminobenzoate, homosalate (3,3,5-trimethylcyclohexyl salicylate); triethanolamine salicylate; 2-phenylbenzimidazole-5-sulfonic acid; sulisobenzone (2-hydroxy-4-methoxybenzophenone-5-sulfonic acid); Padimate A (amyl p-dimethylaminobenzoate); Padimate O (octyl p-dimethylaminobenzoate); 4-t-butyl-4'-methoxydibenzoylmethane; the combination of 2-hydroxy-1,4-naphthoquinone with dihydroxyacetone; and menthyl anthranilate.

The nonphotorearranging sunscreen agents for ultraviolet-A (320–400 nm) include the pentyl and 2-ethylhexyl esters of p-dimethylaminobenzoic acid; dioxybenzone; 2-ethylhexyl p-methoxycinnamate; ethyl 4-bis (hydroxypropyl)aminobenzoate; 3,3,5-trimethylcyclohexyl salicylate; 2-ethylhexyl 2-cyano-3,3-diphenylacrylate; 2-ethylhexyl salicylate; 4-t-butyl-4'-methoxydibenzoylmethane and mixtures thereof. Nonphotorearranging sunscreen agents are present in amounts ranging from 1.0% to 20.0%, preferably 4.0% to 15.0% by weight of the total composition.

Examples of customarily used UV-B absorbers include 2-ethylhexyl p-methoxycinnamate; isoamyl p-methoxycinnamate; p-methylbenzylidene-D, L-camphor or its sodium sulfonate, sodium 2-phenylbenzimidazole-5-sulfonate, sodium 3,4-dimethylphenylglyoxylate, phenylbenzophenone, isooctyl 4-phenylbenzophenone-2'-carboxylate, p-methoxycinnamate, 2-phenyl-5-methylbenzoxazole, octyl p-dimethylaminobenzoate, and other p-dimethylaminobenzoate esters.

Preferably, sunscreen agents of the invention, such as the benzoin derivatives of Formula 3, should be stored in a dark container to prevent premature photorearrangement. Most preferably, sunscreen compositions containing benzoin derivatives should be stored in a dark, preferably black, container that significantly limits exposure of the composition to light.

As stated above, benzoin compounds are sensitive to light. Therefore it is helpful to have a stable form of the compound for storage purposes. Benzoin compounds are preferably protected from light by storage as their dithiane derivatives (Formula 2). The dithiane protecting group can be removed by contact with mercuric perchlorate. Removal of the dithiane protecting group gives the benzoin compound (Formula 3). The benzoin compound is converted to the benzofuran compound (Formula 4) by exposure to light.

The generic dithiane adducts depicted in Formula 2, below, represent important, nonphotolabile, intermediate compounds. In one embodiment, the present invention provides novel photolabile precursor compounds as generally depicted in Formula 2:

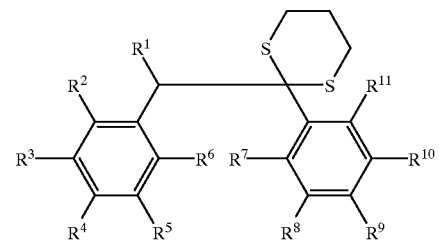

Formula 2

Formula 2. Generic structure for dithiane protected benzoin compounds.

In one embodiment, $R^1$ is hydroxy, carbonate, substituted ester (—OC(O)R), a phosphorus-containing group, a sulfur-containing group, a fluorescent label, or a biomolecule. $R^2$, $R^3$, $R^4$, $R^5$, $R^6$, $R^7$, $R^8$, $R^9$, $R^{10}$, and $R^{11}$ are each hydrogen, alkyl, aryl, alkoxy, substituted alkoxy, or halide. At least one of $R^2$ or $R^6$ is hydrogen. At least one of $R^2$, $R^3$, $R^4$, $R^5$ and $R^6$ is hydroxy or substituted alkoxy.

In addition to the dithiane-benzoin adducts of Formula 2, the present invention provides the corresponding photolabile benzoin compounds, as generically depicted below in Formula 3:

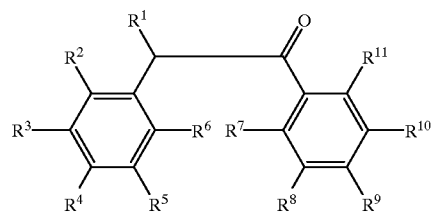

Formula 3. Generic structure of substituted benzoin derivatives.

In this embodiment, $R^1$ is hydroxy, carboxy, substituted ester, a phosphorus-containing group, a sulfur-containing group, or a fluorescent label. $R^2$, $R^3$, $R^4$, $R^5$, $R^6$, $R^7$, $R^8$, $R^9$, $R^{10}$, and $R^{11}$ are each hydrogen, alkyl, aryl, alkoxy, substituted alkoxy, or halide. At least one of $R^2$ or $R^6$ is hydrogen. At least one of $R^2$, $R^3$, $R^4$, $R^5$ and $R^6$ is hydroxy or substituted alkoxy.

The generic compound depicted in Formula 3 is generally made by removing the dithiane adduct to form the ketone. This is accomplished as is generally known in the art, using mercuric perchlorate or bis(trifluoroacetoxy)iodobenzene; see for example Greene et al., *Protective groups in Organic Synthesis*, John Wiley and Sons, New York, 1991, pp. 203–205, hereby incorporated by reference. In this manner, the dithiane adduct serves as a protecting group of the photolabile benzoin, during subsequent manipulations or until photolysis is desired. At the appropriate time, the dithiane adduct is removed, and then photolysis is initiated as needed.

In another embodiment, the present invention includes the corresponding photorearranged benzofuran compounds as generally depicted in Formula 4:

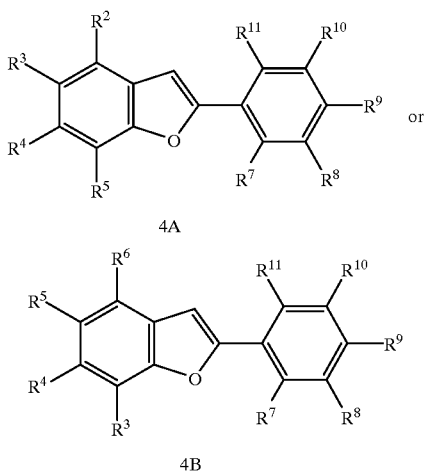

Formula 4. Generic structure for benzofuran compounds.

Isomeric compounds 4A and 4B of Formula 4 differ only in that the firan ring formation occurs at the $R^6$ and $R^2$ positions, respectively. Where, in the benzoin precursor, $R^2$ is hydrogen and $R^6$ is not hydrogen, 4B will be formed. Where, in the benzoin precursor, $R^6$ is hydrogen and $R^2$ is not hydrogen, 4A will be formed. Where, in the benzoin precursor, both $R^2$ and $R^6$ are hydrogen, a mixture of 4A and 4B will be formed. In this last case, 4A and 4B will be identical compounds unless $R^3$ and $R^5$ in the benzoin precursor are different (see FIG. 1, compounds 8 and 9).

In this embodiment $R^2$, $R^3$, $R^4$, $R^5$, $R^6$, $R^7$, $R^8$, $R^9$, $R^{10}$, and $R^{11}$ are each hydrogen, alkyl, aryl, alkoxy, substituted alkoxy, or halide. At least one of $R^2$, $R^3$, $R^4$, $R^5$ and $R^6$ is hydroxy or substituted alkoxy.

The furan products (Formula 4) are formed from the substituted benzoins after exposure to light. Formula 1 depict the furan formed by attack at the $R^2$ (4B) or $R^6$ (4A) positions, one of which are necessarily hydrogen.

The following functional group definitions further describe the preferred embodiments of the structures described herein.

By "carbonate" herein is meant a —OC(O)OH or —OC(O)OR$^{12}$ group. $R^{12}$ may be hydrogen, alkyl, aryl, amine, secondary alkyl amine, tertiary alkyl amine, alkoxy, a biomolecule, or a fluorescent label.

By "substituted ester" herein is meant a —OC(O)R$^{12}$ group, where $R^{12}$ may be hydrogen, alkyl, aryl, amine, secondary alkyl amine, tertiary alkyl amine, alkoxy, a biomolecule, or a fluorescent label. Thus, the $R^1$ may be a carbamate of the formula —OC(O)NR'R", where R' and R" may be the same or different and include hydrogen, alkyl, and aryl. When $R^1$ is a substituted ester, and $R^{12}$ is an amine group, secondary amines are preferred.

By "alkyl" or "alkyl group" or grammatical equivalents herein is meant a straight or branched chain alkyl group, with straight chain alkyl groups being preferred. If branched, it may be branched at one or more positions, and unless specified, at any position. Also included within the definition of an alkyl group are cycloalkyl groups such as C5 and C6 rings. In some cases, two R groups may be part of the same ring structure, that is, they may be linked to form a cyclic structure, including heterocyclic structures. For example, as described in Pillai, Synthesis, January 1980, pp. 1–26, incorporated herein by reference, $R^3$ and $R^4$ and/or $R^9$ and $R^{10}$ may be joined to form a methylene dioxy, five-membered ring; in addition, $R^2$ and $R^3$, and/or $R^7$ and $R^8$, may also be similarly joined. In some cases, the R groups may form an aryl group; for example, as described in U.S. Pat. No. 4,469,774, $R^9$ and $R^{10}$ may form a benzyl group, such that a naphthyl group is formed.

The alkyl group may range in size from about 1 to 100 carbon atoms (C1–C100), with a preferred embodiment utilizing from about 1 to about 20 carbon atoms (C1–C20), with about C1 through about C8 being most preferred. However, in some embodiments, the alkyl group may be larger, particularly if it is a straight chain alkyl. Particularly preferred compounds have methyl groups in the $R^2$ to $R^{11}$ positions.

By "aryl" or "aryl group" herein is meant aromatic rings including phenyl, benzyl, and naphthyl, as well as heterocyclic aromatic rings such as pyridine, furan, thiophene, pyrrole, indole and purine, and other heterocyclic aromatic rings containing carbon, nitrogen, oxygen, sulfur, or phosphorus.

The alkyl and aryl groups may be substituted; for example, a phenyl group may be a substituted phenyl group. Suitable substitution groups include, but are not limited to, alkyl groups; aryl groups; halogens such as chlorine, bromine and fluorine; amines; carboxylic acids; and nitro groups.

By the term "amine" herein is meant an —NR$^{13}$R$^{14}$ group. In this embodiment, $R^{13}$ and $R^{14}$ may be the same or different, and may be hydrogen, alkyl or aryl. A preferred —NR$^{13}$R$^{14}$ group is —NH$_2$. A secondary amine is —NR$^{13}$R$^{14}$ where either $R^{13}$ or $R^{14}$, but not both, is hydrogen. A tertiary amine is —NR$^{13}$R$^{14}$ where neither $R^{13}$ nor $R^{14}$ is hydrogen.

By "hydroxy" herein is meant an —OH group.

By "alkoxy" herein is meant an —OR$^{15}$ group, where $R^{15}$ is an alkyl group as defined above. Included within the definition of alkoxy is methoxy (—OCH$_3$).

By "substituted alkoxy" herein is meant a —OXC(R$^{16}$)(R$^{17}$)(R$^{18}$) group, wherein X is either not present (i.e. substituted methoxy) or a straight or branched chain alkyl group. In a preferred embodiment, X is a straight chain alkyl group, such that the substituted alkoxy group has the formula —O(CH$_2$)$_n$C(R$^{16}$)(R$^{17}$)(R$^{18}$), wherein n is 0 (substituted methoxy, which is preferred) or greater, preferably from 0 to 100, with 0 to 20 being especially preferred. $R^{16}$, $R^{17}$ and $R^{18}$ are selected from the group consisting of hydrogen, amino, carboxy, phosphorus-containing groups, sulfur-containing groups, protecting groups such as silyl groups and others known in the art, biomolecules, or fluorescent labels. In a preferred embodiment, $R^{16}$ and $R^{17}$ are hydrogen, such that there is a single substitution group.

By "phosphorus-containing group" herein is meant a finctional group containing at least one phosphorus atom. In a preferred embodiment, the phosphorus-containing group is chemically or functionally active, such that further groups may be attached to the compound using the phosphate. In a preferred embodiment, the phosphorus-containing group is a phosphate (—OP(O)(OH)$_2$) group, a pyrophosphate group, or a substituted phosphate group of the formula —OP(O)(OR$^{19}$)(OR$^{20}$). In this embodiment, $R^{19}$ and $R^{20}$ include, but are not limited to, hydrogen, alkyl, or aryl. In a preferred embodiment, one of $R^{19}$ and $R^{20}$ is hydrogen. Also included within the definition of phosphorus-containing groups are phosphines (—RPR$^{19}$R$^{20}$), and phosphonates (—R—P(O)(OR$^9$)(OR$^{20}$)).

By "sulfur-containing group" herein is meant a functional group containing at least one sulfur atom. As for the phosphates, the sulfur-containing group is preferably chemically or functionally active, such that further groups such as biomolecules may be attached using the sulfur atom. Thus thiols (—RSH), sulfides (—RSR$^{19}$), sulfoxides (—RS(O)R$^{19}$), sulfones (—RS(O)$_2$R$^{19}$), sulfates (—ROS(O)$_2$OR$^{19}$), and sulfonic acids (—RS(O)$_2$OH) are all included within the definition of sulfur-containing groups.

By "halide" herein is meant a halide atom. Preferred halides include chlorine, fluorine, bromine, and iodine, with chlorine and fluorine being particularly preferred, and chlorine being most preferred.

As is shown above, the compounds of Formulas 2, 3, and 4 have many possible structures varying by the functionality of the substituents used. Preferred R groups for Formulas 2, 3, and 4 are as follows. R$^1$ can be hydroxy, carbonate, substituted ester (—OC(O)R), phosphorus-containing group, a sulfur-containing group, a fluorescent label, or a biomolecule. Preferably, R$^1$ is carbonate, carboxyl, phosphate, sulfate, amine salt (—NR$_3^+$), and halide. More preferably, R$^1$ is —OC(O)OEt. R$^2$ can be hydrogen, alkyl, aryl, alkoxy, or substituted alkoxy. Preferably, R$^2$ is hydrogen. R$^3$ can be hydrogen, alkyl, aryl, alkoxy, or substituted alkoxy. Preferably, R$^3$ is alkoxy, substituted alkoxy, or—if R$^5$ is alkoxy or substituted alkoxy—hydrogen. More preferably R$^3$ is —OMe. R$^4$ can be hydrogen, alkyl, aryl, alkoxy, or substituted alkoxy. Preferably, R$^4$ is hydrogen. R$^5$ can be hydrogen, alkyl, aryl, alkoxy, or substituted alkoxy. Preferably, R$^5$ is alkoxy or substituted alkoxy. More preferably R$^5$ is —OMe. R$^6$ can be hydrogen, alkyl, aryl, alkoxy, or substituted alkoxy. Preferably, R$^6$ is hydrogen. R$^7$ can be hydrogen, alkyl, aryl, alkoxy, or substituted alkoxy. Preferably, R$^7$ is hydrogen. R$^8$ can be hydrogen, alkyl, aryl, alkoxy, or substituted alkoxy. Preferably, R$^8$ is hydrogen. R$^9$ can be hydrogen, alkyl, aryl, alkoxy, or substituted alkoxy. Preferably, R$^9$ is hydrogen. R$^{10}$ can be hydrogen, alkyl, aryl, alkoxy, or substituted alkoxy. Preferably, R$^{10}$ is hydrogen. R$^{11}$ can be hydrogen, alkyl, aryl, alkoxy, or substituted alkoxy. Preferably, R$^{11}$ is hydrogen.

Preferred embodiments of the invention have at least one hydrogen as either R$^2$ or R$^6$ in Formulas 2 and 3. This is required due to the photolysis mechanism depicted in Equation 1, wherein a furan ring is formed by attack at either the R$^2$ or R$^6$ position. Accordingly, at least R$^2$ or R$^6$ must be hydrogen; i.e. either R$^2$ or R$^6$ must not contain a substitution group. In a preferred embodiment, both R$^2$ and R$^6$ in Formulas 2 and 3 are hydrogen.

The dithiane-benzoin adducts of Formula 2, and the substituted benzoin compounds of Formula 3 are generally synthesized using the scheme depicted in FIG. 1. Generally, the synthesis comprises contacting the reactants depicted below in Formula 5 (for the formation of Formula 2 compounds):

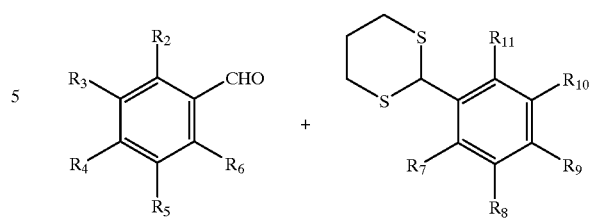

Formula 5. Starting materials for the formation of photoresponsive benzoins.

This is done under conditions that allow the formation of the dithiane-benzoin adducts described herein.

Generally, the hydroxy group of hydroxybenzaldehyde is protected, using a known protecting group such as a tert-butyldimethylsiloxy group. A dithiane adduct is added, using the Corey-Seebach dithiane addition, to form a dithianebenzoin compound (FIG. 1, Compound 2). The hydroxyl protecting group is removed, and a chemically-active group is added. For example, a substituted alkoxy can be added. The substituted alkoxy can be altered to include a chemically reactive group such as a carboxy group (FIG. 1, Compound 4), or a carbamate (FIG. 1, Compound 5) at one of the R$^2$ through R$^6$ positions. In a similar manner an amino group, a phosphorus-containing group, a sulfur-containing group, a substituted carbonyl, a biomolecule, a label, or others may be added to the benzyl ring, as is known in the art.

When a biomolecule is to be added to the benzyl or benzoyl ring, or at the R$^1$ position, it may be done in a variety of ways depending on the biomolecule. Generally, when a biomolecule is to be attached to the core compound, it is done in two stages. First, the core compound is made containing two chemically active groups; one at the R$^1$ position, and one at one of the other R groups. For example, the core compound is made with amines, carboxy groups, phosphate groups, or sulfhydryl groups, for example. Next, the biomolecule or label is made, which also contains a functional group that can be used for attachment. In some instances, other reactive groups of the biomolecule or label are protected to prevent them from reacting with the functional group of the core compound. For example, amino acid side chains containing amino groups, such as arginine, may need to be protected to prevent the side chain from reacting, although in some embodiments the attachment is done via a functional group of an amino acid side chain. Protecting groups and techniques are well known in the art. Once the core compound and the biomolecule or label are made, they can be attached by reacting with the functional groups.

EXAMPLES

General: THF was refluxed over sodium and benzophenone, and was distilled prior to use. 3-hydroxybenzaldehyde (Fluka) was dissolved in diethyl ether, filtered through a plug of neutral alumina, and evaporated. All other starting materials were from Aldrich and used without further purification. The 1.0 M tetrabutylammonium fluoride (TBAF) solution in THF was dried over 3 Å molecular sieves. IR spectra were acquired from a thin film of the sample on a polyethylene substrate.

Example 1

Synthesis of 3-(tert-butyldimethylsilyloxy)benzaldehyde (FIG. 1, Compound 1)

The hydroxyl of 3-hydroxybenzaldehyde was protected as the TBDMS ether, to circumvent dianion solubility problems. To a solution of 3-hydroxybenzaldehyde (12.21 g, 100 mmol) in 600 mL THF was added t-butyldimethylsilyl chloride (TBDMSCl, 18.84 g, 125 mmol). The solution was cooled to 0° C. and triethylamine (12.65 g, 17.4 mL, 125 mmol) was added dropwise. The reaction mixture was brought to room temperature and stirred 5 hours. The mixture was filtered and the THF removed under reduced pressure. The oil was repeatedly dissolved in 200 mL portions of THF and evaporated until no more triethylamine hydrochloride precipitated. The oil was then dissolved in 150 mL diethyl ether, filtered through a plug of neutral alumina and activated charcoal to remove the salt and the yellow color, and evaporated. The colorless, mobile oil was dried in vacuo overnight. Yield: 21.43 g (91%). IR: 1703, 1583, 1482, 1278, 1145, 840 cm$^{-1}$. $^1$H NMR (CDCl$_3$, TMS)d 9.927 (s, 1 H), 7.447 (d,J=7.50 Hz, 1 H), 7.379–7.335 (m, 2 H), 7.096–7.074 (m, 1 H), 0.994 (s, 9 H), 0.215 (s, 6 H). $^{13}$C NMR (CDCl$_3$, TMS) d 191.60, 156.34, 138.03, 130.03, 126.34, 123.46, 119.70, 25.59, 18.12, −4.52. Anal. Calcd for C$_{13}$H$_{20}$O$_2$Si: C, 66.05; H, 8.53. Found: C, 66.13; H, 8.53.

Example 2

Synthesis of (±)-1-hydroxy-1-(3-tert-butyldimethylsilyloxyphenyl)-2-phenyl-2-(1,3-dithian-2-yl)-ethane (FIG. 1, Compound 2)

A solution of 2-phenyl-1,3-dithiane (15.71 g, 80 mmol) in 125 mL THF was prepared. The solution was treated at 0° C. under a nitrogen atmosphere with 40 mL of n-butyllithium (2.0 M in cyclohexane, 80 mmol). After 30 min, 3-(tert-butyldimethylsilyloxy)benzaldehyde (18.91 g, 80 mmol) was added. The solution was stirred for 1 hr at 0° C., then poured into 100 mL of 1 N HCl and extracted with dichloromethane (4×50 mL). The organic phase was washed with brine, dried with Mg$_2$SO$_4$, filtered through a plug of activated charcoal and silica gel, and evaporated under reduced pressure. The resulting oil was crystallized from ethanol/water to form a white powder. Yield: 28.98 g (84%). mp 75–76° C. IR: 3449 (br), 1601, 1484, 1275, 1152, 834 cm$^{-1}$. $^1$H NMR (CDCl$_3$, TMS) d 7.70 (d, J=7.50 Hz, 2 H), 7.308–7.235 (m, 3 H), 6.937 (t, J=7.79 Hz, 1 H), 6.682–6.660 (m, 1 H), 6.427–6.404 (m, 2 H), 4.926 (d, J=3.73 Hz, 1 H), 2.936 (d,J=3.76 Hz, 1 H), 2.739–2.610 (m, 4 H), 1.942–1.879 (m, 2 H), 0.935 (s, 9 H), 0.111 (s, 6 H). $^{13}$C NMR (CDCl$_3$, TMS) d 154.43, 138.89, 137.47, 130.42, 128.00, 127.69, 127.36, 121.23, 119.89, 119.54, 80.74, 66.36, 27.22, 26.93, 25.65, 24.69, 18.03, −4.40. Anal. Calcd. C$_{23}$H$_{32}$O$_2$S$_2$Si: C, 63.84; H, 7.45. Found: C, 63.83; H, 7.26.

Example 3

Synthesis of (±)-1-hydroxy-1-(3-carbomethoxymethoxyphenyl)-2-phenyl-2-(1,3-dithian-2-yl)-ethane (FIG. 1, Compound 3)

The phenolic hydroxyl was conveniently and selectively alkylated by treatment with TBAF in the presence of methyl bromoacetate, to yield the methyl ester. A solution of (±)-1-hydroxy-1-(3-tert-butyldimethylsilyloxyphenyl)-2-phenyl-2-(1,3-dithian-2-yl)-ethane (28.12 g, 65 mmol) and methyl bromoacetate (12.43 g, 81.25 mmol) in 150 mL dry THF was prepared under a nitrogen atmosphere. The solution was treated with 1 M TBAF in THF (68.25 mL, 68.25 mmol) dropwise. The solution was allowed to react overnight, then was poured into ethyl acetate (200 mL) and washed with water (5×50 mL). The organic phase was dried with Mg$_2$SO$_4$ and evaporated. The residue was dissolved in 200 mL diethyl ether, filtered through a small quantity of neutral alumina and activated charcoal, and dried in vacuo. The product was crystallized from ethyl acetate/hexanes, to afford a white powder. Yield: 23.61 g (93%). mp 122–122.5° C. IR: 3471 (br), 1760, 1595, 1441, 1211, 714 cm$^{-1}$. $^1$H NMR (CDCl$_3$, TMS) d 7.679 (dd, J=8.16, 1.55 Hz, 2 H), 7.265–7.325 (m, 3 H), 7.045 (t, J=7.92 Hz, 1 H), 6.804–6.782 (m, 1 H), 6.553 (d, J=7.61 Hz, 1 H), 6.302 (s, 1 H), 4.960 (d, J=3.51 Hz, 1 H), 4.367 (s, 2 H), 3.778 (s, 3 H), 3.023 (d, J=3.52 Hz), 2.757–2.620 (m, 4 H), 1.951–1.891 (m, 2 H). $^{13}$C NMR (CDCl$_3$, TMS)d 169.17, 156.61, 138.88, 137.40, 130.46, 128.08, 127.98, 127.49, 121.76, 115.35, 113.68, 80.73, 66.32, 52.11, 27.30, 26.99, 24.74. Anal. Calcd. for C$_{20}$H$_{22}$O$_4$S$_2$: C, 61.51; H, 5.68. Found: C, 61.34; H, 5.75.

Example 4

Synthesis of (±)-1-hydroxy-1-(3-carboxymethoxyphenyl)-2-phenyl-2-(1,3-dithian-2-yl)-ethane (FIG. 1, Compound 4)

A solution of anhydrous lithium iodide (2.68 g, 20 mmol, Aldrich) in 25 mL dry pyridine was brought to reflux under a nitrogen atmosphere and treated with (±)-1-hydroxy-1-(3-carbomethoxymethoxyphenyl)-2-phenyl-2-(1,3-dithian-2-yl)-ethane (1.95 g, 5 mmol). The reaction was refluxed for 6 h, then allowed to cool to room temperature under a stream of nitrogen. The solution was poured into 1 N HCl (300 mL), and extracted with ethyl acetate (3×50 mL). The combined ethyl acetate layers were extracted with 5% sodium bicarbonate (4×50 mL). The aqueous phase was acidified to pH 2, and extracted with ethyl acetate (3×50 mL). The organic phase was dried with Mg$_2$SO$_4$, filtered through activated charcoal, evaporated, and triturated with hexanes to yield a white solid. Yield: 1.71 g (91%). mp 99–101° C. IR: 3448 (br), 1735, 1595, 1462, 1232, 719 cm$^{-1}$. $^1$H NMR (CDCl$_3$, TMS) d 7.656 (dd, J=8.00, 1.71 Hz, 2 H), 7.299–7.254 (m, 3 H), 7.036 (t, J=7.98 Hz, 1 H), 6.794–6.773 (m, 1 H), 6.573 (d, J=7.55 Hz, 1 H), 6.251 (s, 1 H), 4.955 (s, 1 H), 4.357 (s, 2 H), 2.728–2.620 (m, 4 H), 1.914–1.868 (m, 2 H). $^{13}$C NMR (CDCl$_3$, TMS) d 173.47, 156.32, 139.01, 137.40, 130.50, 128.12, 128.07, 127.56, 122.02, 115.43, 113.66, 80.56, 66.13, 64.73, 27.26, 26.96, 24.67. Anal. Calcd. for C$_{19}$H$_{20}$O$_4$S$_2$: C, 60.62; H, 5.35. Found: C, 60.36; H, 5.21.

Example 5

Synthesis of (±)-1-hydroxy-1-(3-carbamylmethoxyphenyl)-2-phenyl-2-(1,3-dithian-2-yl)-ethane (FIG. 1, Compound 5)

A solution of (±)-1-hydroxy-1-(3-carboxymethoxyphenyl)-2-phenyl-2-(1,3-dithian-2-yl)-ethane (391 mg, 1 mmol) was prepared in 50 mL methanol with gentle warming. The solution was cooled to 0° C., and gaseous ammonia was bubbled through for 30 min. The flask was wrapped in a towel, securely stoppered, and allowed to come to room temperature. After 2 h, the solvent was removed under reduced pressure to yield a white solid. Yield: 348 mg (93%). mp 140–141° C. IR: 3460, 3346 (br), 1680, 1586, 1442, 1252, 1058, 714 cm$^{-1}$. $^1$H NMR (CDCl$_3$, TMS) d 7.686 (dd, J=7.82, 1.70 Hz, 2 H), 7.336–7.291 (m, 3 H), 7.088 (t, J=7.93 Hz, 1 H), 6.774 (dd, J=8.09, 2.55 Hz, 1 H), 6.626 (d, J=7.67 Hz, 1 H), 6.463 (s, br, 1 H), 6.335 (s, 1 H), 5.582 (s, br, 1 H), 4.971 (d, J=3.16 Hz, 1 H), 4.245 (s, 2 H), 3.092 (d J=3.24 Hz, 1 H), 2.777–2.635 (m, 4 H), 1.962–1.905 (m, 2 H). $^{13}$C NMR (CDCl$_3$, TMS) d 170.699, 156.059, 139.293, 137.529, 130.437, 128.245, 127.696, 122.261, 114.772, 114.270, 80.706, 67.077, 66.462, 27.342, 27.002, 24.729. Anal. Calcd. for C$_{19}$H$_{21}$NO$_3$S$_2$: C, 60.77; H, 5.64; N, 3.73. Found: C, 60.93; H, 5.79; N, 3.76.

Example 6

Synthesis of (±)-1-acetoxy-1-(3-carbamylmethoxyphenyl)-2-phenyl-2-(1,3-dithian-2-yl)-ethane (FIG. 1, Compound 6)

To a solution of (±)-1-hydroxy-1-(3-carbamylmethoxyphenyl)-2-phenyl-2-(1,3-dithian-2-yl)- ethane (192 mg, 0.5 mmol) in 10 mL THF was added DMAP (2 mg), triethylamine (70 mL, 0.5 mmol), and acetic anhydride (94 mL, 1.0 mmol). The solution was stirred at room temperature for 4 h, and then partitioned between ethyl acetate (50 mL) and 5% sodium bicarbonate (50 mL). The organic phase was washed with water (3×50 mL), dried with $Mg_2SO_4$, and evaporated to yield a colorless oil. Yield 205 mg (98%). IR: 3479, 3331 (br), 1747, 1694, 1589, 1443, 1224, 1033, 910, 718 cm$^{-1}$. $^1$H NMR (CDCl$_3$, TMS) d 7.740 (dd, J=8.15, 1.55 Hz, 2 H), 7.348–7.281 (m, 3 H), 7.111 (t, J=7.96 Hz, 1 H), 6.801 (dd, J=8.18, 2.53 Hz, 1 H), 6.686 (d, J=7.59Hz, 1 H), 6.521 (s, 2 H), 6.312 (s, 1 H), 6.136 (s, 1 H), 4.238 (s, 2 H), 2.751–2.597 (m, 4 H), 2.104 (s, 3 H), 1.933–1.857 (s, 1 H). $^{13}$C NMR (CDCl$_3$, TMS) d 171.080, 169.318, 156.012, 136.974, 130.771, 128.402, 128.045, 127.738, 122.586, 115.072, 114.635, 79.890, 66.982, 63.133, 27.270, 27.109, 24.568, 20.848. Anal. Calcd. for $C_{21}H_{23}NO_4S_2$: C, 60.41; H, 5.55; N, 3.35. Found: C, 59.92; H, 5.76; N, 3.14.

Example 7

Synthesis of (±)-O-acetyl-3'-carbamylmethoxybenzoin (FIG. 1, Compound 7)

To a solution of (±)-1-acetoxy-1-(3-carbamylmethoxyphenyl)-2-phenyl-2-(1,3-dithian-2-yl)-ethane (110 mg, 0.26 mmol) in 5 mL 9:1 (v/v) acetonitrile/water was added mercuric perchlorate (148 mg, 0.33 mmol). The solution was stirred for 15 min, filtered through a 0.45 mm PTFE syringe filter (Gelman) into a 5% sodium bicarbonate solution (10 mL), and extracted with 50 mL dichloromethane. The organic phase was dried and evaporated under reduced pressure to yield a colorless oil. Samples for analysis were evaporated from methanol, dissolved in warm water and lyophilized. Yield: 65 mg (76%). IR: 3445, 1743, 1694, 1462, 1236, 1075, 720 cm$^{-1}$. $^1$H NMR (CDCl$_3$, TMS) d 7.936 (d, J=7.82 Hz, 2 H), 7.529 (t, J=7.56 Hz, 1 H), 7.412 (t, J=7.57 Hz, 2 H), 7.319 (t, J=7.86 Hz, 1 H), 7.139 (d, J=7.51 Hz, 1 H), 7.051 (s, 1 H), 6.884 (dd, J=8.21, 2.75 Hz, 1 H) 6.835 (s, 1 H), 6.558 (s, 1 H), 6.148 (s, 1 H), 4.462 (s, 2 H), 2.207 (s, 3 H). $^{13}$C NMR (CDCl$_3$, TMS) d 193.577, 170.825, 170.348, 157.593, 135.473, 134.494, 133.637, 130.516, 128.768, 128.711, 122.371, 115.205, 115.140, 77.144, 67.115, 20.715. Anal. Calcd. for $C_{18}H_{17}NO_5 \cdot H_2O$: C, 62.59; H, 5.54; N, 4.05. Found: C, 62.53; H, 5.12; N, 3.90.

Steady-state photolysis of (±)-O-acetyl-3'-carbamylmethoxybenzoin

A 47.7 mM solution of (±)-O-acetyl-3'-carbamylmethoxybenzoin in 1:1 methanol/Tris·HCl (0.05 M, pH 7.40) was prepared in a 1-cm pathlength quartz cuvette. The sample was irradiated by an Oriel 66011 Hg vapor lamp operating at 450 watts, filtered with a water-cooled Schott glass UG11 filter. At intervals, the sample was removed, and the UV absorption spectrum from 210–400 nm taken by a HP 8452 spectrophotometer. Complete photolysis occurred within a 90 sec exposure.

For isolation of the photoproduct, a 25.6 mg sample of (±)-O-acetyl-3'-carbamylmethoxybenzoin in 50 mL methanol was irradiated in 3 mL batches as above, until no further change was observed in the absorption spectrum of the sample. The methanol was removed under reduced pressure to yield 20.6 mg (99%) of the photoproduct. The composition of this material was 74% 2-phenyl-5-carbamylmethoxybenzofuran, 24% 2-phenyl-7-carbamylmethoxybenzofuran, and 2% other material, as determined by GCMS. Standard samples were obtained by preparative TLC (silica gel/diethyl ether) of the crude photolyzed sample, and identified by $^1$H NMR and IR.

Transient photolysis of (±)-O-acetyl-3'-carbamylmethoxybenzoin

A 9.54 mM solution of (±)-O-acetyl-3'-carbamylmethoxybenzoin in 1:1 methanol/Tris·HCl (0.05 M, pH 7.40) was prepared in a 1-cm pathlength quartz cuvette. The sample was photolyzed using the third harmonic at 355 nm from a Q-switched Spectra Physics DCR-12 Nd:YAG laser. Typical pulses were 10–20 ns (FWHM) in duration at an energy of 1.5 mJ/pulse. The sample was monitored with a 75-W xenon arc lamp filtered with a Schott glass UG11 filter placed between the arc lamp and the cuvette. The probe light exiting the cuvette was then wavelength selected by a SA 1690B double monochromator set at 310 nm, and was detected with a photomultiplier. The signal was amplified with a Keithly 427 current amplifier, and digitized by a Tektronix R$_7$10 200 MHz transient digitizer interfaced to a microcomputer. Samples were acquired at a 10 Hz photolysis pulse repetition rate, and scans represented the average of 20 pulses.

Irradiation of (±)-O-acetyl-3'-carbamylmethoxybenzoin resulted in a clean conversion to the phenylbenzofurans (FIG. 1, Compounds 8 and 9). Steady-state photolysis spectra of (±)-O-acetyl-3'-carbamylmethoxybenzoin show two isosbestic points throughout the course of the photolysis (FIG. 3). The two isomeric photoproducts, Compounds 8 and 9 of FIG. 1, were produced in a 98% yield at a ratio of 3:1 as determined by GCMS and NMR of the isolated phenylbenzofurans, along with an equivalent of acetic acid.

Due to the large absorption change at 310 nm ($\Delta\epsilon=35,000$ M$^{-1}$ cm$^{-1}$), transient absorption studies of the formation of the benzofurans were performed. Quenching studies by Sheehan et al. supra, showed that photolysis of 3',5'-dimethoxybenzoin acetate is extremely rapid, with a rate on the order of $10^{10}$ sec$^{-1}$. Rapid photolysis seems to have been preserved in the (±)-O-acetyl-3'-carbamylmethoxybenzoin. Photolysis of (±)-O-acetyl-3'-carbamylmethoxybenzoin with a frequency tripled Nd:YAG laser at 355 nm resulted in a rapid absorption increase at 310 nm. The course of this increase could not be measured within the instrument response time of approximately 30 ns, which places a lower limit on the photolysis rate of $3\times10^7$ sec$^{-1}$ (data not shown).

Example 8

Dithiane-protected 3',5'-dimethoxybenzoin

A solution of 2-phenyl-1,3-dithiane (390 mg, 2 mM) in 20 mL of dry THF was cooled to 0° C. and 1.01 equivalents of nBuLi was added dropwise via syringe with rapid stirring. This solution was allowed to stir for 30 minutes and then 1.0 equivalents of 3,5-dimethoxybenzaldehyde dissolved in 1 ml dry THF was added dropwise. The solution was allowed to warm to room temperature and stir for 1 hr. The reaction was quenched by the addition of aqueous NH$_4$Cl, THF solvent is removed in vacuo and the resultant slurry extracted with dichloromethane. The dichloromethane layer was washed with 2×20 mL of water and solvent removed in vacuo to yield a pale yellow oil. The obtained oils typically crystallize upon standing and are greater than 99% pure based on GC/MS. H$^1$ NMR and TLC. As such, they can be used for further synthetic transformations without purification.

Example 9

Dithiane-protected 4'-methoxybenzoin

The procedure in Example 8 was followed except that 1.0 equivalent of 4-methoxybenzaldehyde was used in place of the 3,5-dimethoxybenzaldehyde.

Example 10

Dithiane-protected 2'-ethoxybenzoin

The procedure in Example 8 was followed except that 1.0 equivalent of 2-ethoxybenzaldehyde was used in place of the 3,5-dimethoxybenzaldehyde.

Example 11

Dithiane-protected 2'-methylbenzoin

The procedure in Example 8 was followed except that 1.0 equivalent of 2-methylbenzaldehyde was used in place of the 3,5-dimethoxybenzaldehyde.

Example 12

Synthesis of 3',5'-dimethoxybenzoinyl ethyl carbonate

A solution of 3.927 g (20 mmol) 2-phenyl-1,3-dithiane in 100 mL dry THF under a nitrogen atmosphere at 0° C. was prepared. N-butyllithium (8 mL, 2.5 M in hexanes, 20 mmol) was added dropwise over 5 minutes, and the solution stirred for one-half hour. Solid 3,5-dimethoxybenzaldehyde (3.324 g, 20 mmol) was then added. After one-half hour, ethyl chloroformate (2.713 g, 25 mmol) was added. Additional THF was added (100 mL), followed by a solution of 18.42 g (41 mmol) mercuric perchlorate dissolved in a minimal quantity of water. After 15 minutes, a solution of 5.560 g $K_2CO2_3$ in Inimal water was added and the mixture filtered through a plug of silica gel. Diethyl ether (200 mL) was added to the filtrate and the solution extracted with 5% (w/v) $NaHCO_3$ and brine. The organic layer was dried with $Mg_2SO_4$ and evaporated. Crystallization from diethyl ether/hexanes afforded 6.04 g (88%) of the title compound. This material was recrystallized from diethyl ether to yield 4.20 g (61%) of analytically pure material. $^1$H-NMR ($CDCl_3$, TMS) δ 7.938 (m, 2 H), 7.523 (m, 1 H), 7.404 (m, 2 H), 6.654 (s, 1 H), 6.615 (d, J=2.2 Hz, 2 H), 6.409 (t, J=2.2 Hz, 1H), 4.228 (q, J=6.3 Hz, 2 H) 3.744 (s, 6 H), 1.323 (t, J=2.2 Hz, 3 H).

The foregoing description details specific methods which can be employed to practice the present invention. Having detailed such specific methods, those skilled in the art will well enough know how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

We claim:

1. A composition for variably blocking radiation comprising:

(A) a first sunscreen agent capable of undergoing an intramolecular photochemical rearrangement to form a second sunscreen agent wherein the second sunscreen agent can absorb more ultraviolet radiation per molecule than the first sunscreen agent; and (B) a carrier for topical administration.

2. A composition according to claim 1 wherein the first sunscreen agent is a benzoin derivative.

3. A sunscreen composition comprising:
(A) a compound having the formula

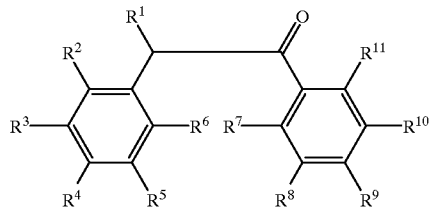

wherein
$R_1$ is hydroxy, carbonate, substituted ester (—OC(O)R), phosphorus-containing group, a sulfur-containing group, a fluorescent label, or a biomolecule;
$R_2$ is hydrogen, alkyl, aryl, alkoxy or substituted alkoxy;
$R_3$ is hydrogen, alkyl, aryl, alkoxy or substituted alkoxy;
$R_4$ is hydrogen, alkyl, aryl, alkoxy or substituted alkoxy;
$R_5$ is hydrogen, alkyl, aryl, alkoxy or substituted alkoxy;
$R_6$ is hydrogen, alkyl, aryl, alkoxy or substituted alkoxy;
$R_7$ is hydrogen, alkyl, aryl, alkoxy or substituted alkoxy;
$R_8$ is hydrogen, alkyl, aryl, alkoxy or substituted alkoxy;
$R_9$ is hydrogen, alkyl, aryl, alkoxy or substituted alkoxy;
$R_{10}$ is hydrogen, alkyl, aryl, alkoxy or substituted alkoxy;
$R_{11}$ is hydrogen, alkyl, aryl, alkoxy or substituted alkoxy;
wherein at least one of $R^2$ or $R^6$ is hydrogen;
wherein at least one of $R^2$, $R^3$, $R^4$, $R^5$, or $R^6$ is hydroxy or substituted alkoxy; and
(B) a carrier for topical administration.

4. A sunscreen composition comprising:
(A) an ultraviolet-absorbing compound having the formula

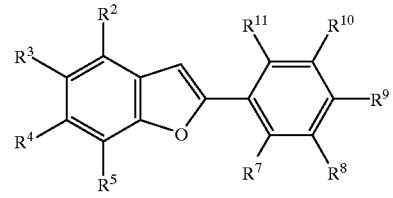

wherein
$R_2$ is hydrogen, alkyl, aryl, alkoxy or substituted alkoxy;
$R_3$ is hydrogen, alkyl, aryl, alkoxy or substituted alkoxy;
$R_4$ is hydrogen, alkyl, aryl, alkoxy or substituted alkoxy;
$R_5$ is hydrogen, alkyl, aryl, alkoxy or substituted alkoxy;
$R_7$ is hydrogen, alkyl, aryl, alkoxy or substituted alkoxy;
$R_8$ is hydrogen, alkyl, aryl, alkoxy or substituted alkoxy;

$R_9$ is hydrogen, alkyl, aryl, alkoxy or substituted alkoxy;
$R_{10}$ is hydrogen, alkyl, aryl, alkoxy or substituted alkoxy;
$R_{11}$ is hydrogen, alkyl, aryl, alkoxy or substituted alkoxy;
wherein at least one of $R^2$, $R^3$, $R^4$, or $R^5$ is hydroxy or substituted alkoxy; and
(B) a carrier for topical administration.

5. A composition useful for blocking ultraviolet radiation comprising:

(A) a compound having the formula

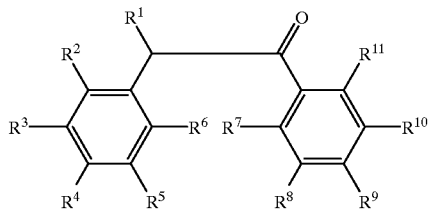

wherein
$R_1$ is selected from the group consisting of carbonate, carboxyl, phosphate, sulfate, amine salt (—N(R)$_3^+$), and halide;
$R_2$ is selected from the group consisting of hydrogen, alkyl, aryl, alkoxy, and substituted alkoxy;
$R_3$ is selected from the group consisting of hydrogen, alkyl, aryl, alkoxy, and substituted alkoxy;
$R_4$ is selected from the group consisting of hydrogen, alkyl, aryl, alkoxy, and substituted alkoxy;
$R_5$ is selected from the group consisting of hydrogen, alkyl, aryl, alkoxy, and substituted alkoxy;
$R_6$ is selected from the group consisting of hydrogen, alkyl, aryl, alkoxy, and substituted alkoxy;
$R_7$ is selected from the group consisting of hydrogen, alky, aryl, alkoxy, and substituted alkoxy;
$R_8$ is selected from the group consisting of hydrogen, alkyl, aryl, alkoxy, and substituted alkoxy;
$R_9$ is selected from the group consisting of hydrogen, alkyl, aryl, alkoxy, and substituted alkoxy;
$R_{10}$ is selected from the group consisting of hydrogen, alkyl, aryl, alkoxy, and substituted alkoxy;
$R_{11}$ is selected from the group consisting of hydrogen, alkyl, aryl, alkoxy, and substituted alkoxy;
wherein at least one of $R^2$ or $R^6$ is hydrogen;
wherein at least one of $R^2$, $R^3$, $R^4$, $R^5$ or $R^6$ is hydroxy or substituted alkoxy; and
(B) a carrier for topical administration.

6. A composition according to claim 5 wherein
$R^2$ is hydrogen;
$R^3$ is selected from the group consisting of hydrogen, alkoxy, and substituted alkoxy;
$R^4$ is hydrogen;
$R^5$ is selected from the group consisting of alkoxy and substituted alkoxy;
$R^6$ is hydrogen;
$R^7$ is hydrogen;
$R^8$ is hydrogen;
$R^9$ is hydrogen;
$R^{10}$ is hydrogen; and
$R^{11}$ is hydrogen.

7. A composition according to claim 5 wherein
$R^2$ is hydrogen;
$R^3$ is methoxy;
$R^4$ is hydrogen;
$R^5$ is methoxy;
$R^6$ is hydrogen;
$R^7$ is hydrogen;
$R^8$ is hydrogen;
$R^9$ is hydrogen;
$R^{10}$ is hydrogen; and
$R^{11}$ is hydrogen.

8. A composition according to claim 5 further comprising an auxiliary sunscreen agent having a different ultraviolet absorption maximum than the compound.

9. A composition according to claim 5 further comprising a photorearranged product of the ultraviolet-absorbing compound.

10. A composition useful for blocking ultraviolet radiation comprising:

(A) an ultraviolet-absorbing compound having the formula

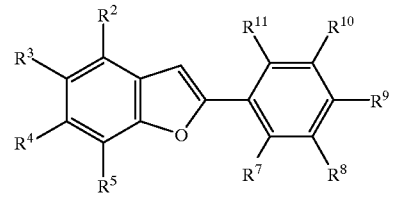

wherein
$R^2$ is selected from the group consisting of hydrogen, alkyl, aryl, alkoxy, and substituted alkoxy;
$R^3$ is selected from the group consisting of hydrogen, alkyl, aryl, alkoxy, and substituted alkoxy;
$R^4$ is selected from the group consisting of hydrogen, alkyl, aryl, alkoxy, and substituted alkoxy;
$R^5$ is selected from the group consisting of hydrogen, alkyl, aryl, alkoxy, and substituted alkoxy;
$R^7$ is selected from the group consisting of hydrogen, alkyl, aryl, alkoxy, and substituted alkoxy;
$R^8$ is selected from the group consisting of hydrogen, alkyl, aryl, alkoxy, and substituted alkoxy;
$R^9$ is selected from the group consisting of hydrogen, alkyl, aryl, alkoxy, and substituted alkoxy;
$R^{10}$ is selected from the group consisting of hydrogen, alkyl, aryl, alkoxy, and substituted alkoxy;
$R^{11}$ is selected from the group consisting of hydrogen, alky, aryl, alkoxy, and substituted alkoxy;
wherein at least one of $R^2$, $R^3$, $R^4$, or $R^5$ is hydroxy or substituted alkoxy; and
(B) a carrier for topical administration.

11. A composition according to claim 10 wherein
$R^2$ is hydrogen;
$R^3$ is selected from the group consisting of hydrogen, alkoxy, and substituted alkoxy;
$R^4$ is hydrogen;
$R^5$ is selected from the group consisting of alkoxy and substituted alkoxy;
$R^7$ is hydrogen;
$R^8$ is hydrogen;
$R^9$ is hydrogen;

$R^{10}$ is hydrogen; and $R^{11}$ is hydrogen.

12. A composition according to claim 10 wherein $R^2$ is hydrogen;

$R^3$ is methoxy;

$R^4$ is hydrogen;

$R^5$ is methoxy;

$R^6$ is hydrogen;

$R^7$ is hydrogen;

$R^8$ is hydrogen;

$R^9$ is hydrogen;

$R^{10}$ is hydrogen; and $R^{11}$ is hydrogen.

13. A composition according to claim 10 further comprising an auxiliary sunscreen agent having a different ultraviolet absorption maximum than the ultraviolet-absorbing compound (A).

14. A method of protecting skin or hair from ultraviolet radiation comprising applying to a skin surface or hair an effective amount of a composition according to any one of claims 5, 6, 7, 8, 9, 10, 11, 12, or 13.

* * * * *